(12) United States Patent
Bettocchi

(10) Patent No.: US 9,801,532 B2
(45) Date of Patent: Oct. 31, 2017

(54) MEDICAL INSTRUMENT

(75) Inventor: Stefano Bettocchi, Bari (IT)

(73) Assignee: Karl Storz GmbH & Co. KG, Tuttlingen (DE)

(*) Notice: Subject to any disclaimer, the term of this patent is extended or adjusted under 35 U.S.C. 154(b) by 1688 days.

(21) Appl. No.: 12/477,702

(22) Filed: Jun. 3, 2009

(65) Prior Publication Data

US 2009/0299134 A1    Dec. 3, 2009

(30) Foreign Application Priority Data

Jun. 3, 2008  (DE) .................. 10 2008 026 457

(51) Int. Cl.
| | |
|---|---|
| *A61B 1/12* | (2006.01) |
| *A61B 1/00* | (2006.01) |
| *A61B 1/015* | (2006.01) |
| *A61M 1/00* | (2006.01) |
| *A61M 39/10* | (2006.01) |
| *A61M 39/12* | (2006.01) |

(52) U.S. Cl.
CPC ........... *A61B 1/12* (2013.01); *A61B 1/00128* (2013.01); *A61B 1/015* (2013.01); *A61M 1/0064* (2013.01); *A61M 39/105* (2013.01); *A61M 39/12* (2013.01); *A61M 2039/1077* (2013.01); *A61M 2039/1094* (2013.01); *A61M 2205/6045* (2013.01)

(58) Field of Classification Search
USPC ........ 600/156, 132, 134, 131, 152, 158–159
See application file for complete search history.

(56) References Cited

U.S. PATENT DOCUMENTS

| | | | |
|---|---|---|---|
| 5,133,336 A | 7/1992 | Savitt et al. | |
| 5,447,148 A * | 9/1995 | Oneda et al. | 600/158 |
| 5,518,501 A | 5/1996 | Oneda et al. | |
| 6,511,230 B1 * | 1/2003 | Connelly et al. | 385/58 |
| 8,348,524 B2 * | 1/2013 | Iwamizu et al. | 385/89 |
| 2002/0098732 A1 * | 7/2002 | Shimizu | 439/352 |
| 2005/0191046 A1 * | 9/2005 | Dehmel et al. | 396/17 |

(Continued)

FOREIGN PATENT DOCUMENTS

| | | |
|---|---|---|
| DE | 19805532 A1 | 8/1998 |
| DE | 20011409 U1 | 10/2000 |

(Continued)

OTHER PUBLICATIONS

German Search Report; Application No. 10 2008 026 457.1; dated Nov. 11, 2008; 4 pages.

(Continued)

*Primary Examiner* — Timothy J Neal
(74) *Attorney, Agent, or Firm* — Whitmyer IP Group LLC

(57) ABSTRACT

A medical instrument for endoscopic procedures that is provided with a hollow shaft, such that at least two channels are configured in the shaft and the channels can be coupled on the proximal end with supply conduits. To create a medical instrument of the aforementioned type which is of simple structure and ensures secure connect ability, it is proposed according to the invention that the proximal end of at least one first channel positioned in the shaft and the distal end at least one supply conduit that is to be coupled with this first channel are configured with respect to their geometric structural design in such a way that this first channel and the corresponding supply conduit can be coupled only with one another.

14 Claims, 2 Drawing Sheets

(56) References Cited

U.S. PATENT DOCUMENTS

| | | | |
|---|---|---|---|
| 2006/0135851 A1* | 6/2006 | Yamazaki | 600/159 |
| 2006/0270904 A1* | 11/2006 | Kupferschmid et al. | 600/131 |
| 2007/0043262 A1* | 2/2007 | Levy et al. | 600/156 |
| 2007/0186660 A1* | 8/2007 | Francisco et al. | 73/715 |

FOREIGN PATENT DOCUMENTS

| | | |
|---|---|---|
| DE | 102005024352 A1 | 12/2006 |
| EP | 1728527 A2 | 12/2006 |
| EP | 1800596 A1 | 6/2007 |
| JP | 2007252834 A | 10/2007 |

OTHER PUBLICATIONS

European Search Report; EP 09 00 5616; dated Aug. 7, 2009; 6 pages.

* cited by examiner

MEDICAL INSTRUMENT

CROSS-REFERENCE TO RELATED APPLICATIONS

The present application claims priority of German patent application No. 10 2008 026 457.1 filed on Jun. 2, 2008, the content of which is incorporated herein by reference.

FIELD OF THE INVENTION

The invention relates to a medical instrument for endoscopic procedures, which is provided with a hollow shaft so that at least two channels are configured in the shaft and the channels can be coupled with supply conduits at the proximal end. In addition the invention relates to a handle for a medical instrument.

BACKGROUND OF THE INVENTION

Endoscopic instruments with at least one channel configured in the handle are known in various models in the art. The channels are configured, for instance, as suction, irrigation, and light conducting channels, with the suction and irrigation channels serving to clean the surgical area and the endoscope lens while the light conducting channel is used to convey sufficient light for endoscopic examinations and interventions into the surgical area by means of light conductors.

In connecting the channels of the handle with the external supply conduits, to ensure that the correct channels and supply conduits are always coupled with one another, it is common in the art to provide the channels/supply conduits with matching color codings, arrows, and/or other markings. Especially in the often hectic activity of a clinic, however, this type of connection labeling does not constitute sufficient protection against erroneous connections of the channels.

U.S. Pat. No. 5,518,501 A discloses a medical instrument in which the supply conduits that are to be coupled with the channels of the handle are joined together in an adapter which in turn can be secured to the handle. With this medical instrument that is known in the art, the adapter is configured as a component that is adapted to the shape of the handle and can be coupled only with handles of this special form. This configuration ensures a very high protection against erroneous connection, but the cost of building it is very high and demands in each case a handle of totally determined form.

Consequently it is the object of the invention to create a medical instrument of the aforementioned type which is of simple construction and ensures a high degree of connection security.

SUMMARY OF THE INVENTION

This object is fulfilled according to the invention in that the proximal end of the at least one first channel situated in the shaft and the distal end of at least one supply conduit that is to be coupled with this first channel, with respect to its geometric structural design, are configured in such a way that this first channel and the corresponding supply conduit can be coupled exclusively with one another.

As a result of the individual geometrical structural design of the proximal and distal ends, to be connected to one another, of the channels positioned in the shaft and of the supply conduits, a maximum of connection security is obtained because only channels and supply conduits of equal structural shape can be coupled with one another. With the inventive design, erroneous connection is excluded because channels and supply conduits that do not match one another cannot be connected with one another.

With this medical instrument it is sufficient to adapt only the proximal ends of the channels positioned in the shaft and the distal ends of the supply conduits to one another structurally and geometrically, without the necessity of adapting the entire medical instrument to the supply conduits.

According to a preferred embodiment of the invention it is proposed that the proximal ends of all channels positioned in the medical instrument, as well as the distal ends of all supply conduits, should be configured in such a way in terms of their geometric structural design that each channel of the medical instrument can be coupled exclusively with the correspondingly geometrically and structurally designed supply conduit.

To facilitate coupling of the channels on the instrument side with the supply conduits, it is proposed with a practical embodiment of the invention that several supply conduits should be combined in a connecting adapter that can be coupled with the medical instrument, so that the connecting adapter can be advantageously secured to the medical instrument by means of a coupling mechanism.

According to a practical embodiment of the invention it is proposed that the coupling mechanism should be configured as a catch connection, for instance with a catch hook and a corresponding catch recess for the rest hook.

To configure the geometrical shape that individualizes the ends of the channels/supply conduits, it is proposed according to a first inventive embodiment that the channels/supply conduits are adapted to one another in terms of their inner and outer diameter and/or their cross-sectional shape in the area of their ends that are to be coupled to one another.

In addition or alternatively to the adaptation of the cross-sectional shapes and/or diameters, according to a second inventive embodiment it is proposed that the channels of the medical instrument and the supply conduits that are gathered together in a connecting adapter should be adapted to one another in terms of their length in the area of their ends that are to be coupled together.

Finally it is proposed with the invention that in at least one channel of the medical instrument or in at least one supply conduit, a return valve or dosing valve should be configured in order to be able to vary the suction and/or irrigating capacity and to exclude fluid streams in the wrong direction.

In addition the invention relates to a handle for a medical instrument for endoscopic interventions, where in the handle that bears the shaft at least two channels are configured that extend outside the shaft and the channels positioned in the handle can be coupled with supply conduits on the proximal end.

To prevent errors in coupling the channels positioned in the handle with the supply conduits, it is proposed with the invention that the proximal end of at least one first channel positioned in the handle and the distal end of at least one supply conduit to be coupled with this first channel of the handle should be configured for purposes of their geometric constructive design in such a way that this first channel and the corresponding supply conduit can be coupled exclusively with one another.

To facilitate coupling of the channels of the handle with the supply conduits, it is proposed with a practical embodiment of the invention that several supply conduits should be brought together in a connecting adapter that can be coupled with the handle, so that the connecting adapter advantageously can be secured on the handle by means of a coupling mechanism.

According to a practical embodiment of the invention, it is proposed that the coupling mechanism should be configured as a catch connection, for instance with a catch hook and a corresponding catch recess for the catch hook.

In addition to the known suction and/or irrigation channels, video connections and electrical connections such as HF connections are also considered to be channels and supply conduits in the context of this invention.

Further characteristics and advantages of the invention can be seen with reference to the associated illustrations in which an embodiment of an inventive medical instrument is depicted only in exemplary manner, without restricting the invention to this embodiment.

DETAILED DESCRIPTION OF THE INVENTION

Figure 1:
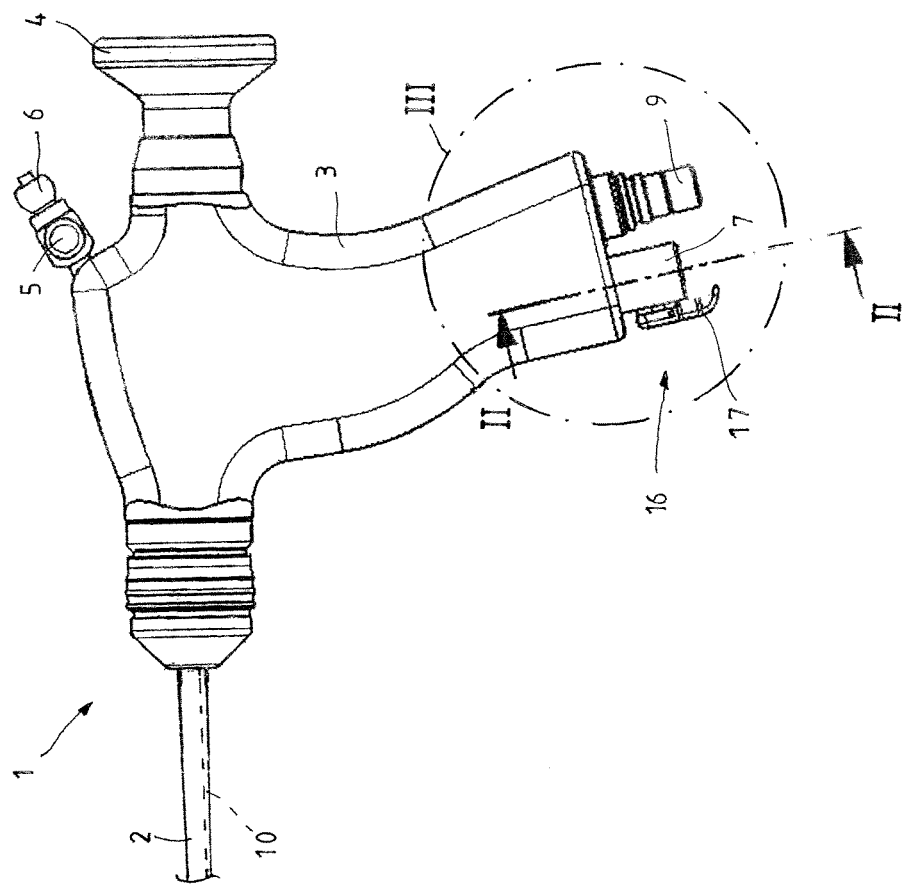
FIG. 1 shows a schematic side view of an inventive medical instrument in uncoupled position.
Figure 2:
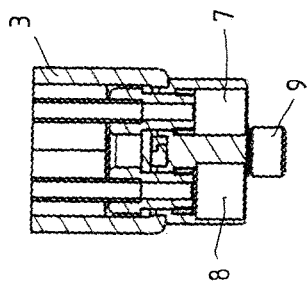
FIG. 2 shows a section along the line II-II according to FIG. 1.

FIG. 1 shows an endoscope 1 that consists basically of a hollow shaft 2 and a handle 3 that supports the shaft 3. To examine the surgical area as well as to control instruments during the intervention, the endoscope 1 comprises an optical system made up of various lenses that ends on the proximal end in an ocular unit 4.

On the proximal end the endoscope 1, in addition, comprises, in the side view shown in FIG. 1, an access 6 to the hollow shaft 2 that can be closed by means of a valve 5 and by means of which medical instruments, such as cutting and/or gripping instruments, can be inserted into the hollow shaft 2 and finally into the surgical area. The valve 5 serves, when the medical instrument is not inserted, to close the hollow shaft 2 so that it is fluid-tight, for instance to prevent any escape of the gas serving to configure the pneumoperitoneum during laparoscopy.

It is also possible, of course, that the endoscope 1 should have more than just one access 6 for inserting medical instruments into the hollow shaft 2.

As can further be seen from FIGS. 1 through 4, various channels are configured in the handle 3, for instance a suction channel 7, an irrigation channel 8, and a lighting channel 9, which lead into the hollow shaft 2. While the suction channel 7 and the irrigation channel 8 as a rule lead freely into the hollow shaft 2, the lighting channel 9 at the handle end continues in a lighting channel 10 in the shaft 2.

It is also possible, of course, to configure the hollow shaft 2 in such a way that the suction and irrigation channels 7, 8 on the handle end continue in separate channels in the shaft 2, as well as so that at least one separate working channel is configured in the hollow shaft 2 for receiving the medical instrument or instruments that are inserted by the access 6 or accesses 6 into the hollow shaft 2. Likewise, of course, more than just three channels 7, 8, and 9 can be positioned in the handle 3.

Figure 3:
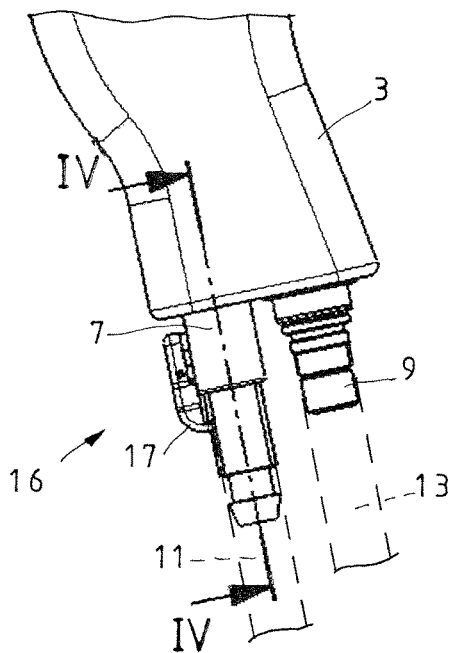
FIG. 3 shows a view of detail III from FIG. 1, but depicting the medical instrument coupled with supply conduits.
Figure 4:
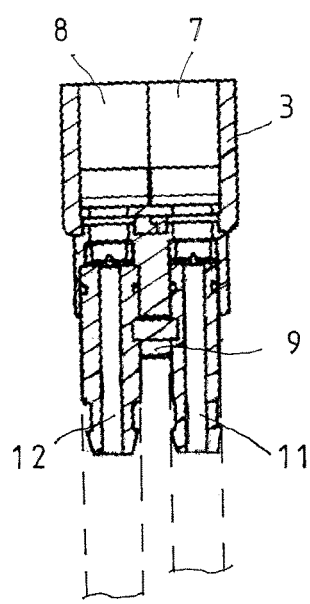
FIG. 4 shows a section along the line IV-IV according to FIG. 3.

To set the endoscope 1 in operation, supply conduits 11, 12, and 13 leading from outside can be connected to the channels 7, 8, and 9 positioned in the handle 3, as is shown in FIGS. 3 and 4.

Video connections and electrical connections such as HF connections can be considered as channels and supply conduits in the meaning of the medical instrument illustrated and described here.

Figure 5:
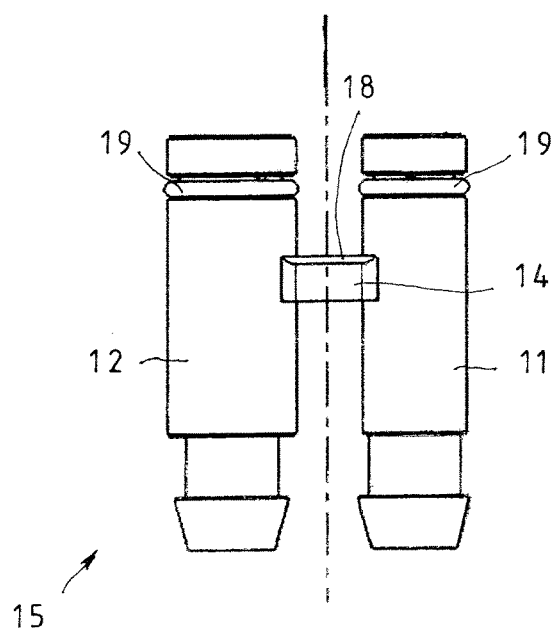
FIG. 5 shows a blown-up depiction of a connecting adapter that is to be coupled with the medical instrument.

As can also be seen from FIGS. 3 through 5, in the illustrated embodiment the suction supply conduit 11 and the irrigation supply conduit 12 are brought together by means of a stud 14 to a connecting adapter 15 so that the two supply conduits 11 and 12 can simultaneously be secured as a one-piece coupling block on the channels 7 and 8 of the handle 3.

In the illustrated embodiment the light supply conduit 13 is configured as a separate supply conduit 13; however, it is also possible, of course, to combine all supply conduits 11, 12, and 13 in one connecting adapter 15.

The connecting adapter 15 is secured to the proximal ends of channels 7 and 8 of the handle 3 by means of a coupling mechanism 16, which in the illustrated embodiment is configured as a catch connection with a catch hook 17 mounted on the handle 3 and with a catching recess 18 configured on the stud 14 for the catch hook 17.

In the embodiment shown in FIG. 5 the supply conduits 11 and 12 comprise insulating elements 19 that are configured as O-rings on the distal end in order to ensure fluid-tight coupling to the channel 7 and 8 of the handle 3. It is also possible, of course, to position the insulating elements 19 on the proximal end of channels 7 and 8 of the handle 3.

To ensure that the correct supply conduit 11, 12, or 13 is always connected to the related channel 7, 8, or 9 of the handle 3—for instance, suction supply conduit 11 to the suction channel 7 of the handle 3 and irrigation supply conduit 12 to the irrigation channel 8 of the handle 3—the proximal end of at least one first channel 7, 8, or 9 positioned in the handle 3 and the distal end of at least one supply conduit 11, 12, or 13 that is to be coupled with this first channel 7, 8, or 9 of the handle 3 is configured with respect to its geometric structural design in such a way that this first channel 7, 8, or 9 and the corresponding supply conduit 11, 12, or 13 can be coupled only with one another.

A geometric structural design of this type can, for instance, be such that the proximal end of a channel 7, 8, or 9 has a triangular structure and the distal end of the supply conduit 11, 12, or 13 that is to be coupled with this channel 7, 8, or 9 is likewise of triangular structure in order to ensure that only these channels and supply conduits that are mutually matched in their design can be coupled with one another.

This individualization of the proximal ends of the channels 7, 8, and/or 9 on the handle end as well as of the distal ends of the related supply conduits 11, 12, and/or 13 ensures that only channels 7, 8, and/or 9 and supply conduits 11, 12, and/or 13 that correspond exclusively to one another concerning the geometric structural design can be coupled with one another, so that any erroneous connection can be ruled out because of the non-matching shape of the counterpart.

To configure the geometry that individualizes the ends of the channels/supply conduits, it is proposed according to a first embodiment that the channels/supply conduits should be adapted to one another with respect to their inner and outer diameter and/or their cross-section shape in the area of their ends that are to be coupled with one another.

Additionally or alternatively to the adaptation of the cross-section shapes and/or diameters, it is proposed according to a second embodiment that the channels 7, 8, and 9 of the handle 3 as well as the supply conduits 11, 12, and 13 that are combined in a connecting adapter 15 in the area of their ends that are to be coupled with one another should be adapted to one another with respect to their length.

An endoscope 1 configured in this way is distinguished in that, along with a simple structure, a maximum of connection security is ensured concerning the connection of the channels 7, 8, and 9 positioned in the handle 3 with the related supply conduits 11, 12, and 13.

What is claimed is:

1. A medical instrument for endoscopic procedures comprising:
    a handle and a hollow shaft,
    wherein in the handle that supports the hollow shaft at least two channels are configured extending from the shaft and the channels positioned in the handle able to be coupled on the proximal end with supply conduits,
    wherein the proximal end of at least one first channel positioned in the handle and the distal end of at least one supply conduit that is to be coupled with this first channel of the handle are configured in such a way with respect to their geometric structural design that the first channel and the corresponding supply conduit are able to be coupled only with one another,
    wherein at least two supply conduits are combined by means of a stud, which is arranged connective between the at least two supply conduits to one connecting adapter that are able to be secured to the handle by means of a coupling mechanism, and
    wherein the coupling mechanism is configured as a catch connection with the stud being configured as a part of the catch connection.

2. The medical instrument of claim 1, wherein the proximal ends of all channels of the handle as well as the distal ends of all supply conduits are configured in such a way with respect to their geometric structural design that every channel can be coupled only with the correspondingly constructed geometrically designed supply conduit.

3. The medical instrument of claim 2, wherein several supply conduits are combined in a connecting adapter that can be coupled with the proximal ends of the channels of the handle.

4. The medical instrument of claim 1, wherein the channels of the handle and the supply conduits in the area of their ends that are to be coupled are adapted to one another concerning their inner or outer diameters and/or their cross-sectional form.

5. The medical instrument of claim 1, wherein the channels of the handle as well as the supply conduits combined in a connecting adapter are adapted to one another with respect to their length in the area of their ends that are to be mutually coupled.

6. The medical instrument of claim 1, wherein a check valve or dosing valve is positioned in at least one channel of the medical instrument or supply conduit.

7. The medical instrument of claim 1, wherein the channels of the medical instrument as well as the supply conduits combined in a connecting adapter are adapted to one another with respect to their length in the area of their ends that are to be mutually coupled.

8. A medical instrument for endoscopic procedures comprising:
    a hollow shaft, said hollow shaft comprising at a first channel and a second channel, each said channel having a proximal end;
    a first supply conduit and a second supply conduit, each said supply conduit having a distal end,
    wherein said proximal end of said first channel is able to be coupled to said distal end of said first supply conduit, and said proximal end of said second channel is able to be coupled to said distal of said second supply conduit,
    wherein said first channel and said first supply conduit are configured in such a way with respect to their geometric structural design so that said proximal end of said first channel is not able to be coupled with said distal end of said second supply conduit,
    wherein the first and second supply conduits are arranged connective by means of a stud between the first and second supply conduits.

9. The medical instrument of claim 8,
    said hollow shaft further comprising a third channel, said third channel having a proximal end;
    a third supply conduit, said third supply conduit having a distal end;
    wherein said proximal end of said third channel can be coupled to said distal end of said third supply conduit;
    wherein said third channel and said third supply conduit are configured in such a way with respect to their geometric structural design so that said proximal end of said third channel cannot be coupled with one or more of said distal ends of said first supply conduit and said second supply conduit.

10. The medical instrument of claim 8 further comprising:
    a connecting adapter that can be coupled with the medical instrument;
    wherein said first and second supply conduits are combined in said connecting adapter.

11. The medical instrument of claim 10, said connecting adapter further comprising one or more coupling mechanisms;
    wherein said connecting adapter is secured to said proximal ends of the channels of the handle through said one or more coupling mechanisms.

12. The medical instrument of claim 11, wherein said coupling mechanism is configured as a catch connection.

13. The medical instrument of claim 8, wherein a check valve or dosing valve is positioned in at least one channel of said medical instrument or is positioned in at least one supply conduit.

14. The medical instrument of claim 8 further comprising:
    a handle for supporting said hollow shaft;
    wherein said first and second channels extend through a least a portion of said handle.

* * * * *